(12) United States Patent
Little et al.

(10) Patent No.: US 7,408,094 B2
(45) Date of Patent: Aug. 5, 2008

(54) PROCESS FOR THE PRODUCTION OF OLEFINS

(75) Inventors: Ian Raymond Little, Thames Ditton (GB); Ian Allan Beattie Reid, Southfields (GB)

(73) Assignee: Ineos Europe Limited, Hampshire (GB)

( * ) Notice: Subject to any disclaimer, the term of this patent is extended or adjusted under 35 U.S.C. 154(b) by 606 days.

(21) Appl. No.: 10/538,123

(22) PCT Filed: Nov. 18, 2003

(86) PCT No.: PCT/GB03/04993

§ 371 (c)(1),
(2), (4) Date: Jun. 7, 2005

(87) PCT Pub. No.: WO2004/054945

PCT Pub. Date: Jul. 1, 2004

(65) Prior Publication Data
US 2006/0149113 A1     Jul. 6, 2006

(30) Foreign Application Priority Data
Dec. 18, 2002  (GB) ................... 0229497.3

(51) Int. Cl.
*C07C 4/01*  (2006.01)
(52) U.S. Cl. .................. 585/653; 585/324; 585/651; 585/652; 585/658
(58) Field of Classification Search .............. 585/32, 585/651–653, 658
See application file for complete search history.

(56) References Cited

U.S. PATENT DOCUMENTS

| | | | |
|---|---|---|---|
| 3,692,862 A | 9/1972 | Staud et al. | |
| 4,166,830 A | 9/1979 | Guth et al. | |
| 4,264,435 A | 4/1981 | Read, Jr. et al. | |
| 4,349,432 A | 9/1982 | Rowe et al. | |
| 4,527,003 A | 7/1985 | Okamoto et al. | |
| 4,655,904 A | 4/1987 | Okamoto et al. | |
| 4,754,095 A | 6/1988 | Coughenour et al. | |
| 4,952,743 A | 8/1990 | Come | |
| 5,214,226 A | 5/1993 | Bauer et al. | |
| 6,395,944 B1 | 5/2002 | Griffiths et al. | |
| 6,433,234 B1 | 8/2002 | Griffiths et al. | |
| 7,074,977 B2 * | 7/2006 | Rapier et al. ............ | 585/324 |

FOREIGN PATENT DOCUMENTS

| | | |
|---|---|---|
| EP | 0 332 289 A2 | 9/1989 |
| EP | 0 336 823 A1 | 10/1989 |
| EP | 0 983 790 A2 | 3/2000 |
| EP | 1 112 241 B1 | 2/2003 |
| GB | 794157 | 4/1958 |
| GB | 921 305 A | 3/1963 |
| GB | 2 227 249 A | 7/1990 |
| WO | WO 00/14036 | 3/2000 |
| WO | WO 02/04389 * | 1/2002 |

OTHER PUBLICATIONS

*Chemical Week*; pp. 72-73; Jan. 23, 1965.
Sampson, R.J.; "The Reaction Between Ethane and Oxygen at 600-630°"; pp. 5095-5106 (1963).
Asinger, F.; "Mono-olefins: chemistry and technology"; pp. 80-88 (1968).
Calderbank, P.H., et al; "The Autothermic Cracking of Light Hydrocarbons"; *J. Applied Chemistry*; vol. 7; pp. 425-431; Aug. 1957.
Rabitz, H., et al; "Optimal control of methane conversion to ethylene"; *Journal of Physical Chemistry A*; 104/46; pp. 10740-10746 (abstract).
Ross, J.R.H., et al; "Catalytic conversion of methane to higher hydrocarbon(s) by exothermal reaction—coupled with endothermal conversion of hydrocarbon(s) and carbon dioxide or stream in second reactor in heat exchange contact with first reactor"; NL 9300168 (abstract).

(Continued)

*Primary Examiner*—Glenn Caldarola
*Assistant Examiner*—In Suk Bullock
(74) *Attorney, Agent, or Firm*—Nixon & Vanderhye

(57) ABSTRACT

A process for the production of olefins from a hydrocarbon comprising the steps of: a) passing a first feed stream comprising gaseous reactants to a first reaction zone wherein said gaseous reactants react exothermically to provide a product stream b) producing a mixed feed stream comprising oxygen by passing the product stream produced in step (a) and a second feed stream comprising a hydrocarbon feedstock to a mixing zone, oxygen being passed to the mixing zone via (i) the product stream produced in step (a), (ii) the second feed stream comprising a hydrocarbon feedstock and/or (iii) a third stream comprising an oxygen-containing gas c) passing the mixed feed stream directly to an essentially adiabatic second reaction zone wherein in the absence of a supported platinum group metal catalyst at least a part of the oxygen is consumed and a stream comprising olefins is produced e) cooling the stream comprising olefins exiting the second reaction zone to less than 650° C. within less than 150 milliseconds of formation and wherein the temperature of the mixed stream is at least 500° C., the mixing zone and the second reaction zone are maintained at a pressure of between 1.5-50 bar and the residence time within the mixing zone is less than the autoignition delay for the mixed stream.

10 Claims, No Drawings

OTHER PUBLICATIONS

"Ethylene and Propylene Prodn.—By Cold-Flame Oxidation of Butane with Air in Two/Stage Reactor"; SU-1255616 (abstract).

"Prodn. Of Propylene—By Oxidn. Of Propane in Two / Stage Process Using Higher Temp. In Sec. Stage"; SU-1348329 (abstract).

"Unsatd. Hydrocarbons production—from petrol-ligroin fraction by two—stage pyrolysis with partial intermediate cooling"; SU-518141 (abstract).

"Thermally cracking hydrocarbon(s)—involves supplying cracked oil from $1^{st}$ reactor into $2^{nd}$ internally heated at higher temperature"; JP-60235890 (abstract).

"Decomposing raw hydrocarbon material to ethylene—by burning in presence of oxygen, passing mixture to high temperature zone and then cooling"; JP-56034790 (abstract).

"Heating methane cracking reactor—involves use of combustion exhaust gas in combustion of further fuel"; JP-89017043 (abstract).

* cited by examiner

PROCESS FOR THE PRODUCTION OF OLEFINS

This application is the U.S. National Phase of International Application PCT/GB2003/004993, filed 18 Nov. 2003, which designated the U.S. PCT/GB2003/004993 claims priority to British Application No. 0229497.3 filed 18 Dec. 2002. The entire content of these applications are incorporated herein by reference.

The present invention relates to a process for the production of olefins.

Olefins such as ethylene and propylene may be produced by the catalytic dehydrogenation or cracking of a hydrocarbon feed. In this application the term "cracking" will be used to embrace both these chemical reactions. In an auto-thermal cracking process, a hydrocarbon feed is mixed with an oxygen-containing gas and contacted with a catalyst capable of supporting combustion beyond the fuel rich limit of flammability. The hydrocarbon feed is partially combusted and the heat produced is used to drive the cracking reaction.

An example of an auto-thermal cracking process is described in EP 0 332 289. The document describes the use of a paraffinic feed of, for example, ethane, propane and/or butane which is mixed with oxygen and cracked to produce an olefinic mixture. The cracking reaction is endothermic and is carried out at elevated temperatures.

The energy required for the cracking reaction is provided by combustion of a part of the feed and the feed may also be preheated but the temperature is limited due to the risk of autoignition.

Alternatively the energy required may be provided by a preliminary heat-generating step. In this step a gaseous fuel reacts with oxygen in an exothermic reaction in the presence of a catalyst. The reaction conditions are controlled to ensure that not all of the oxygen is consumed during this process. The thermal energy produced by the reaction heats the unreacted oxygen, thereby providing an additional source of heat to drive the cracking of the hydrocarbon feedstock. This process is described in EP 1 112 241.

However using a catalyst to promote the autothermal cracking process can be problematic because the catalyst is prone to deactivate and consequently needs to be periodically replaced or reactivated. The catalyst may also provide a variable performance. Furthermore the catalyst may cause blockages in the reactor system.

It has now been found that an autothermal cracking process can be carried out in the substantial absence of a catalyst.

According to the present invention there is provided a process for the production of olefins from a hydrocarbon said process comprising the steps of:

a) passing a first feed stream comprising gaseous reactants to a first reaction zone wherein said gaseous reactants react exothermically to provide a product stream b) producing a mixed feed stream comprising oxygen by passing the product stream produced in step (a) and a second feed stream comprising a hydrocarbon feedstock to a mixing zone and wherein oxygen is passed to the mixing zone via one or more of (i) the product stream produced in step (a), (ii) the second feed stream comprising a hydrocarbon feedstock and (iii) a third stream comprising an oxygen-containing gas c) passing the mixed feed stream directly to an essentially adiabatic second reaction zone wherein in the absence of a supported platinum group metal catalyst at least a part of the oxygen is consumed and a stream comprising olefins is produced d) cooling the stream comprising olefins exiting the second reaction zone to less than 650° C. within less than 150 milliseconds of formation and wherein the temperature of the mixed stream is at least 500° C., the mixing zone and the second reaction zone are maintained at a pressure of between 1.5-50 bar and the residence time within the mixing zone is less than the autoignition delay for the mixed stream.

Additional feed streams comprising at least one from carbon monoxide, carbon dioxide, steam and hydrogen may also be passed to the mixing zone.

Preferably an additional feed stream comprising hydrogen is passed to the mixing zone.

The gaseous reactants in the first feed stream may be any reactants that are capable of reacting exothermically. The heat generated from the exothermic reaction is transferred to the mixed stream via the resultant product stream produced in step (a).

The gaseous reactants may comprise a gaseous fuel and an oxygen-containing gas.

The gaseous fuel may be any gaseous fuel which is capable of reacting with oxygen in an exothermic reaction. Suitable examples include hydrocarbons, such as methane, ethane, propane and butane. Methane is the preferred gaseous fuel. Other suitable fuels include hydrogen, carbon monoxide, alcohols (e.g. methanol, ethanol), oxygenates and/or ammonia. Waste fuel streams may also be employed.

The oxygen-containing gas may comprise air, oxygen and/or an air/oxygen mixture. The oxygen-containing gas may be mixed with an inert gas such as nitrogen, helium or argon.

The first reaction zone may contain an ignition source such as a pilot flame or a spark ignition source which is used to initiate the exothermic reaction. Alternatively the first reaction zone may comprise a catalyst.

Wherein the first reaction zone contains a catalyst the catalyst usually comprises an oxidation catalyst such as a supported platinum group metal. Suitable catalyst supports include a range of ceramic and metal supports, with alumina supports being preferred. The support may be in the form of spheres or other granular shapes and may be present as a thin layer or wash coat on another substrate. Preferably the substrate is a continuous multi-channel ceramic structure such as a foam or a regular channelled monolith. In a preferred embodiment, the support comprises a gamma-alumina coated alpha-alumina. Alternatively zirconia or a gamma-alumina coated lithium aluminium silicate foam support may be employed.

The first feed stream may be passed to the first reaction zone at a temperature of up to 800° C., preferably between 200 and 600° C. and reacted at at temperature between 600 and 1400° C., preferably between 700 and 1200° C. and most preferably between 950 and 1100° C.

The first reaction zone may be maintained at any suitable pressure e.g. atmospheric pressure. Usually the first reaction zone is maintained at a pressure of from 1.5 to 50 bara (bar absolute), for example between 1.8 to 50 bara, preferably between 5-50 bara, most preferably between 5 to 30 bara and advantageously between 10-30 bara. It will be understood that the precise pressures employed will vary depending on the specific reaction conditions and gaseous reactants employed.

The first feed stream is usually introduced into the first reaction zone at a gas hourly space velocity (GHSV) of greater than 10,000 h$^{-1}$, preferably above 100,000 h$^{-1}$ and most preferably greater than 300,000 h$^{-}$. It will be understood that the optimum gas hourly space time velocity will depend upon the pressure and nature of the feed composition.

In one embodiment of the invention the product stream produced in step (a) may comprise oxygen. Consequently the first feed stream may comprise a gaseous fuel and an oxygen-containing gas which may be passed to the first reaction zone wherein a product stream comprising unreacted oxygen is produced. The product stream may then be passed to the mixing zone to provide the mixed feed stream comprising oxygen.

When the product stream comprising unreacted oxygen is produced the first feed stream comprising a gaseous fuel and an oxygen containing gas is preferably fuel-rich with a fuel to oxygen ratio above the stoichiometric ratio required for complete combustion. For example, the fuel to oxygen ratio in the feed may be 1.5 to 4 times, preferably 3 times the stoichiometric ratio required for complete combustion to carbon dioxide and water.

The gaseous fuel and oxygen-containing gas may be contacted in the first reaction zone under reaction conditions which are controlled to ensure that some of the oxygen in the first feed stream remains unreacted. The thermal energy produced in step (a) heats the unreacted oxygen thereby providing part of the heat necessary for cracking the hydrocarbon feedstock in step (c).

The reaction between the gaseous fuel and oxygen-containing gas may be a combustion reaction. Accordingly, gaseous fuel in the first feed stream may react with oxygen to produce a product stream comprising oxides (e.g. carbon oxides) and water. In such an embodiment and wherein the first reaction zone contains a catalyst, a combustion catalyst is employed. Suitable combustion catalysts include Group VIII metals such as platinum and/or palladium. The catalyst may comprise 0.1 to 5 wt % and preferably 0.25 to 3 wt % of metal. It will be understood that the metal loadings of the catalyst may be selected to ensure that not all the oxygen in the first feed stream is consumed in step (a).

In an alternative embodiment the gaseous fuel of the first feed stream reacts with the oxygen-containing gas to produce synthesis gas. In this embodiment a first feed stream comprising a hydrocarbon (e.g. methane) is employed which reacts with oxygen to produce carbon monoxide and hydrogen. These gaseous products may react exothermically, for example with oxygen, thereby providing a further source of heat to drive the cracking reaction in step (c). In this embodiment, and wherein a catalyst is employed the catalyst is one which is capable of supporting a synthesis gas production reaction. Suitable catalysts comprise rhodium, platinum, palladium, nickel or mixtures thereof. Preferably a rhodium catalyst is used. The catalyst may comprise 0.1 to 5 wt % and preferably 0.25 to 3 wt %, of metal. As with combustion catalysts, the metal loadings of the catalyst may be varied to ensure that not all the oxygen in the first feed stream is consumed in step (a).

In a further embodiment, a gaseous fuel is reacted with an oxygen-containing gas in a combustion reaction and another gaseous fuel (which may or may not be the same as the first gaseous fuel) is reacted with an oxygen-containing gas to produce synthesis gas. Both these reactions are exothermic and may provide part of the heat for driving the subsequent cracking reaction in step (c). In at least one of these reactions, however, not all of the oxygen-containing gas employed is consumed. At least part of this unreacted oxygen is consumed in step (c) to produce the olefin product of the present invention.

The product stream produced from step (a) is usually passed to the mixing zone at a temperature of between 900 and 1400° C., preferably between 950 and 1250° C., and most preferably between 1000 and 1200° C.

In another embodiment of the invention the second feed stream may comprise oxygen. The second feed stream comprising oxygen may then be mixed with the product stream produced in step (a) to provide the mixed feed stream comprising oxygen.

The second feed stream may comprise any suitable hydrocarbon and may optionally comprise an oxygen containing gas. For example, gaseous hydrocarbons, heavy hydrocarbons or mixtures thereof may be employed. Suitable gaseous hydrocarbons include ethane, propane, butane and mixtures thereof. Suitable heavy hydrocarbons include naphtha, gas oil, vacuum gas oil, refinery residues, atmospheric residues, vacuum residues and crude and fuel oils. Additional feed components such as hydrogen, nitrogen, carbon monoxide, carbon dioxide and steam may also be included in the second feed stream. Hydrogen and/or carbon monoxide may react with the oxygen present to produce additional heat for driving the cracking process. In the second feed stream, a gaseous hydrocarbon may be alternated with a heavy hydrocarbon, as the hydrocarbon feed stock.

The second feed stream is usually heated to a temperature of 200° C. to 600° C., and preferably to 300° C. to 500° C.

The second feed stream is introduced at a gas hourly space velocity of greater than 10,000 $h^{-1}$, preferably above 20,000 $h^{-1}$ and most preferably greater than 100,000 $h^{-1}$. It will be understood, however, that the optimum gas hourly space time velocity will depend upon the pressure and nature of the feed composition.

The second feed stream comprising a hydrocarbon feedstock and optionally oxygen is contacted with the product stream produced in step (a), which may or may not contain unreacted oxygen, in a mixing zone wherein a mixed feed stream comprising oxygen is produced.

In yet another embodiment of the invention a third feed stream comprising an oxygen-containing gas may be fed to the mixing zone to provide the mixed feed stream comprising oxygen. The oxygen-containing gas may be any oxygen-containing gas as herein described above.

The temperature of the mixed feed stream is at least 500° C., preferably at least 600° C. and most preferably at least 700° C.

The mixing zone is maintained at a pressure of between 1.5 to 50 bara, for example between 1.8 to 50 bara, preferably between 5-50 bara, most preferably between 5 to 30 bara and advantageously between 10-30 bara.

The mixing zone is usually a mixing channel that passes directly into the second reaction zone. The residence time of the mixed feed stream in the mixing zone is less than the autoignition delay of the mixed feed stream. Methods of determining the autoignition delay are known in the art. For example, ASTM 659-78(2000) is the Standard Test Method for Minimum Autoignition Temperature of Liquid Chemicals and may be easily adapted to determine autoignition delay. A description of a suitably adapted method is provided in the article "Spontaneous Ignition of Methane: Measurement and Chemical Model" by I A B Reid, C Robinson and D B Smith, 20th Symposium (International) on Combustion/The Combustion Institute 1984/pp 1833-1843. Under some conditions of temperature and pressure it may be difficult to measure the autoignition delay directly, but the delay can be predicted using data obtained under other conditions, e.g lower temperature. Having a residence time in the mixing zone of less than the autoignition delay of the mixed feed stream ensures that the production of olefins does not commence until the mixed feed stream enters the second reaction zone. This means that there is little consumption of oxygen in the mixing zone, typically less than 5% wt of the oxygen fed to the mixing zone is consumed in the mixing zone.

Typically the residence time within the mixing zone is less than 100 milliseconds, preferably less than 50 milliseconds, most preferably less than 10 milliseconds and advantageously less than 5 milliseconds.

Preferably the mixed feed stream is passed through the mixing zone and into the into the second reaction zone at a velocity of greater than 1 m/s, preferably greater than 3 m/s. These velocities are sufficiently high to prevent flashback into the first reaction zone.

The second reaction zone is essentially adiabatic so that reaction therein occurs without significant amounts of heat entering or leaving the reaction zone. This is achieved by insulating the second reaction zone.

The hydrocarbon feed in the second feed stream may be cracked into olefins such as ethene, propene, butene and pentene or a mixture thereof.

The cracking reaction may be suitably carried out at a temperature of between 600 and 1200° C., preferably between 850 and 1050° C. and most preferably, between 900 and 1000° C. It will be understood that the optimum temperature will depend upon the feed mixture and operating pressure.

The cracking reaction is carried out in the second reaction zone at a pressure of between 1.5 to 50 bara, for example, between 1.8 to 50 bara, preferably between 5-50 bara, most preferably between 5 to 30 bara and advantageously between 10-30 bara. It will be understood that the precise pressures employed will vary depending on the specific reaction conditions and gaseous fuels employed. The use of higher pressures may provide improved stability and may enable a smaller reactor to be employed. Generally, the use of a higher pressure would be used with lower temperatures and higher temperatures with lower pressures.

The second reaction zone does not contain a supported platinum group metal catalyst i.e. a catalyst comprising a metal of Group 10 of the Periodic Table, particularly catalysts comprising platinum, palladium or mixtures thereof. Preferably the second reaction zone does not contain any catalytic material that is capable of supporting combustion beyond the normal fuel rich limit of flammability. Most preferably the second reaction zone does not contain any material that would exhibit any substantial catalytic activity.

The second reaction zone may contain a stabiliser and/or packing materials such porcelain, ceramics, alumina and/or silica that do not exhibit any substantial catalytic activity.

In a preferred embodiment the second reaction zone may contain a grid(s), a perforated plate(s), and/or a baffle plate(s).

In another preferred embodiment of the invention the second reaction vessel may comprises an ignition source such as, for example, a heated gauze which encourages the reaction to occur at a particular location within the vessel.

In a further embodiment the second reaction zone is essentially empty.

In a preferred embodiment of the invention the residence time within the second reaction zone is sufficient to ensure that substantially all the oxygen is consumed.

Typically the residence time within the second reaction zone is less than 100 milliseconds, preferably less than 50 milliseconds and advantageously less than 10 milliseconds.

After the cracking reaction the products are quenched as they emerge from the second reaction zone such that the temperature is reduced to less than 650° C. within less than 150 milliseconds of formation. The formation of the reaction products, particularly olefins, is assumed to begin at the end of the mixing zone and so the quench time is the time between the reactants leaving the mixing zone and the reduction in temperature of the products to below 650° C.

Wherein the pressure of the second reaction zone is maintained at a pressure of between 1.5-2.0 bara usually the products are quenched and the temperature reduced to less than 650° C. within 100-150 milliseconds of formation.

Wherein the pressure of the second reaction zone is maintained at a pressure of between 2.0-5.0 bara usually the products are quenched and the temperature reduced to less than 650° C. within 50-100 milliseconds of formation.

Wherein the pressure of the second reaction zone is maintained at a pressure of between 5.0-10.0 bara usually the products are quenched and the temperature reduced to less than 650° C. within less than 50 milliseconds of formation.

Wherein the pressure of the second reaction zone is maintained at a pressure of between 10.0-20.0 bara usually the products are quenched and the temperature reduced to less than 650° C. within 20 milliseconds of formation.

Finally wherein the pressure of the second reaction zone is maintained at a pressure of greater than 20.0 bara usually the products are quenched and the temperature reduced to less than 650° C. within 10 milliseconds of formation.

This avoids further reactions taking place and maintains a high olefin selectivity.

The products may be quenched using rapid heat exchangers of the type familiar in steam cracking technology. Additionally or alternatively, a direct quench may be employed. Suitable quenching fluids include water and hydrocarbons such as ethane or naphtha.

The present invention usually provides a percentage conversion of hydrocarbon of greater than 40%, preferably greater than 50%, and most preferably greater than 60%.

Furthermore the present invention usually provides a selectivity towards olefins of greater than 20%, preferably greater than 30%, and most preferably greater than 50%.

Any coke produced in the process of the present invention may be removed by mechanical means, or using one of the decoking methods described in EP 0 709 446, incorporated herein by reference.

EXAMPLE 1

A first feed stream comprising the gaseous reactants methane and oxygen was passed to the first reaction zone comprising a promoted palladium catalyst at a temperature of 400° C. wherein gaseous reactants exothermically reacted to provide a synthesis gas product stream. The first reaction zone was maintained at a pressure of 1.8 bara.

The product stream comprising hydrogen, carbon monoxide, carbon dioxide, and water was passed to the mixing zone at a flow rate of 12.54 g/min wherein the hydrogen flow rate was 1.31 g/min, the carbon monoxide flow rate was 9.48 g/min, the carbon dioxide flow rate was 0.75 g/min and the water vapour flow rate was 1.00 g/min. The temperature of the product stream was 1200° C.

A second feed stream comprising ethane and oxygen was passed to the mixing zone at a flow rate of 24.97 g/min wherein the ethane flow rate was 18.80 g/min and the oxygen flow rate was 6.17 g/min. The temperature of the second feed stream was 450° C.

The residence time in mixing channel was less than 5 ms.

The mixed feed stream with a combined temperature of 610° C. was passed directly to the second reaction zone wherein in the absence of a catalyst the oxygen was consumed and the ethane was converted to ethylene. The second reaction zone was also maintained at a pressure of 1.8 bara.

The product stream exiting the second reaction zone at a temperature of 770° C. was cooled using a water quench to 600° C. within less than 50 milliseconds of formation.

The % conversion of ethane was measured a 68.1% and the selectivity towards ethylene was measured at 77.2%.

EXAMPLE 2

A first feed stream comprising the gaseous reactants methane and oxygen was passed to the first reaction zone comprising a promoted palladium catalyst at a temperature of 300° C. and at a flow rate of 41.0 g/min wherein the flow rate of methane was 18.4 g/min and the flow arte of oxygen was 22.6 g/min. The gaseous reactants exothermically reacted to provide a synthesis gas product stream. The first reaction zone was maintained at a pressure of 20 bara.

The product stream comprising hydrogen, carbon monoxide, carbon dioxide, and water was passed to the mixing zone at a flow rate of 40.99 g/min wherein the hydrogen flow rate was 4.30 g/min, the carbon monoxide flow rate was 29.32 g/min, the carbon dioxide flow rate was 4.61 g/min and the water vapour flow rate was 2.76 g/min. The temperature of the product stream was 1200° C.

A second feed stream comprising ethane and oxygen was passed to the mixing zone at a flow rate of 125.37 g/min wherein the ethane flow rate was 100 g/min and the oxygen flow rate was 25.37 g/min. The temperature of the second feed stream was 250° C.

The residence time in mixing channel was less than 5 ms.

The mixed feed stream with a combined temperature of 600° C. was passed directly to the second reaction zone wherein in the absence of a catalyst the oxygen was consumed and the ethane was converted to ethylene. The second reaction zone was also maintained at a pressure of 20 bara.

The product stream exiting the second reaction zone at a temperature of 800° C. was cooled using a water quench to 600° C. within less than 20 milliseconds of formation.

The % conversion of ethane was measured a 61.4% and the selectivity towards ethylene was measured at 32.06%.

COMPARATIVE EXAMPLE

A mixed feed stream comprising hydrogen, oxygen and ethane was passed to the mixing zone at a flow rate of 24.81 g/min wherein the hydrogen flow rate was 0.70 g/min the ethane flow rate was 18.53 g/min and the oxygen flow rate was 5.58 g/min. The temperature of the feed stream was 450° C.

The mixed feed stream was passed directly to reaction zone comprising a supported platinum group metal catalyst wherein oxygen was consumed and the ethane was converted to ethylene. The reaction zone was also at a pressure of 1.8 bara. The product stream exiting the reaction zone was cooled using a water quench to 600° C. within less than 50 milliseconds of formation.

The % conversion of ethane was measured a 67.6% and the selectivity towards ethylene was measured at 79.0%.

It can be seen from the above examples that an autothermal cracking reaction can be operated in the absence of a catalyst and achieve a high hydrocarbon conversion and a high selectivity towards olefins.

The invention claimed is:

1. A process for the production of olefins from a hydrocarbon said process comprising the steps of:
   a) passing a first feed stream comprising gaseous reactants to a first reaction zone wherein said gaseous reactants react exothermically to provide a product stream
   b) producing a mixed feed stream comprising oxygen by passing the product stream produced in step (a) and a second feed stream comprising a hydrocarbon feedstock to a mixing zone and wherein oxygen is passed to the mixing zone via one or more of (i) the second feed stream comprising a hydrocarbon feedstock and (ii) a third stream comprising an oxygen-containing gas
   c) passing the mixed feed stream directly to an essentially adiabatic second reaction zone wherein in the absence of a supported platinum group metal catalyst in a second reaction zone that does not contain any catalytic material that is capable of supporting combustion beyond the normal fuel rich limit of flammability, at least a part of the oxygen is consumed and a stream comprising olefins is produced
   d) cooling the stream comprising olefins exiting the second reaction zone to less than 650° C. within less than 150 milliseconds of formation
   and wherein the temperature of the mixed stream is at least 500° C., the mixing zone and the second reaction zone are maintained at a pressure of between 1.5-50 bar and the residence time within the mixing zone is less than the autoignition delay for the mixed stream.

2. A process as claimed in claim 1 in which an additional feed stream comprising hydrogen is passed to the mixing zone.

3. A process as claimed in claim 1 in which the residence time within the mixing zone is less than 100 milliseconds.

4. A process as claimed in claim 3 in which the residence time within the mixing zone is less than 5 milliseconds.

5. A process as claimed in claim 1 in which the reaction is carried out in the second reaction zone at a pressure of between 5 to 30 bara.

6. A process as claimed in claim 1 in which the second reaction zone does not contain any material that would exhibit any substantial catalytic activity.

7. A process as claimed in claim 6 in which the second reaction zone contains a stabiliser and/or packing material selected from the group comprising porcelain, ceramics, alumina and silica that do not exhibit any substantial catalytic activity.

8. A process as claimed in claim 1 in which the second reactor contains an ignition source.

9. A process as claimed in claim 1 in which the pressure of the second reaction zone is maintained at a pressure of between 5.0-10.0bara and the products are quenched by reducing the temperature to less than 650° C. within less than 500 milliseconds of formation.

10. A process as claimed in claim 1 in which the pressure of the second reaction zone is maintained at a pressure of between 10.0-20.0 bara and the products are quenched by reducing the temperature to less than 650° C. within 20 milliseconds of formation.

* * * * *